United States Patent
Haraguchi

(10) Patent No.: US 6,943,206 B2
(45) Date of Patent: Sep. 13, 2005

(54) ORGANIC/INORGANIC HYBRID HYDROGEL AND MANUFACTURING METHOD THEREFOR

(75) Inventor: Kazutoshi Haraguchi, Chiba (JP)

(73) Assignee: Kawamura Institute of Chemical Research, Sakura (JP)

( * ) Notice: Subject to any disclaimer, the term of this patent is extended or adjusted under 35 U.S.C. 154(b) by 0 days.

(21) Appl. No.: 10/712,995

(22) Filed: Nov. 17, 2003

(65) Prior Publication Data

US 2004/0106722 A1 Jun. 3, 2004

Related U.S. Application Data

(62) Division of application No. 09/864,184, filed on May 25, 2001, now Pat. No. 6,710,104.

(30) Foreign Application Priority Data

May 29, 2000 (JP) ..................................... P2000-158276

(51) Int. Cl.⁷ .............................. C08F 2/22; C08K 9/00
(52) U.S. Cl. ....................... 523/216; 524/827; 524/916; 526/89; 526/303.1
(58) Field of Search .......................... 523/216; 524/827, 524/916; 526/89, 303.1

(56) References Cited

U.S. PATENT DOCUMENTS

| 3,900,378 | A | 8/1975 | Yen et al. .............. 204/159.14 |
|---|---|---|---|
| 4,418,163 | A | 11/1983 | Murakami et al. |
| 4,600,744 | A | 7/1986 | Libor et al. |
| 5,539,019 | A | 7/1996 | Suskind et al. ............. 523/201 |
| 5,556,547 | A | 9/1996 | Kajita |
| 5,849,816 | A | 12/1998 | Suskind et al. ............. 523/201 |
| 5,883,211 | A | 3/1999 | Sassi et al. |
| 5,998,528 | A | 12/1999 | Tsipursky et al. |
| 6,347,246 | B1 | 2/2002 | Perrault et al. |
| 6,562,891 | B1 * | 5/2003 | Tsai et al. .................... 524/445 |
| 6,765,049 | B2 * | 7/2004 | Lorah et al. ................. 524/445 |

FOREIGN PATENT DOCUMENTS

EP    0335653    10/1989

OTHER PUBLICATIONS

Haraguchi, K. et al., "Effects of clay content on the properties of nanocomposite hydrogels composed of poly(n–isopropylacrylamide) and clay," *Macromolecules*, vol. 35, No. 27, pp. 10162–10171.

* cited by examiner

Primary Examiner—Tae H. Yoon
(74) Attorney, Agent, or Firm—Armstrong, Kratz, Quintos, Hanson & Brooks, LLP

(57) ABSTRACT

The present invention provides a novel organic/inorganic hybrid hydrogel which is superior in homogeneity, transparency, mechanical properties, and in swelling and shrinking properties, a manufacturing method therefor, and a dry body of the organic/inorganic hybrid hydrogel which is obtained by removing water from said hydrogel. The organic/inorganic hybrid hydrogel comprises a water soluble polymer (A), a water swelling clay mineral (B) which can be homogeneously dispersed in water, and water (C), and water (C) is included in a three-dimensional network formed by (A) and (B).

8 Claims, 2 Drawing Sheets

ORGANIC/INORGANIC HYBRID HYDROGEL AND MANUFACTURING METHOD THEREFOR

CROSS PREFERENCE TO RELATED APPLICATION

This application is a Divisional Application of prior application Ser. No. 09/864,184 filed May 25, 2001 now U.S. Pat. No. 6,710,104.

BACKGROUND OF THE INVENTION

1. Field of the Invention

The present invention relates to an organic/inorganic hybrid hydrogel, a dry gel body thereof, and a manufacturing methods therefor. The organic/inorganic hybrid hydrogel constituted by three constituents including a water soluble polymer, a water swelling clay mineral which can be homogeneously dispersed in water, and water, has a structure in which water is included in a three-dimensional network formed by the water soluble polymer and the water swelling clay mineral.

2. Description of the Related Art

A gel is a state of matter which is intermediate between solids and liquids, and which consists of a solvent inside a three dimensional network. Gels containing water (hereinafter, referred to as hydrogels or aqueous gels) are important material for living organisms and such hydrogels are used not only in the fields of the pharmaceuticals, medical care, foods, packaging, sanitary goods, and cosmetics, but also in the industrial fields of agriculture, civil engineering, and other industrial fields. (The fields of application of hydrogel products are described in detail in "Gel Handbook" authored by Yoshihisa Nagata and Kanji Kajiwara, published in 1997 by NTS Company).

Hydrogels include at least two constituents, water and a three dimensional network formed by various types of crosslinking. The three-dimensional network can be formed either by organic or inorganic compounds. In a hydrogel constituted by organic polymers, polymers or organic molecules are crosslinked by covalent bonds, hydrogen bonds, ionic bonds, and hydrophobic bonds, and the crosslinking can also be generated by physical entanglement or at crosslinking points of crystallites.

Known examples of organic molecules which form three dimensional networks includes albumen albumin, blood serum albumin, gelatin which forms networks by helix formation, polyacrylate or polystyrene sulfonic acid, which form bridges by coordinate bonds with agarose or alkaline earth metal ions, a two polymer-type (poly cation and poly anion) complex system, fully saponified polyvinyl alcohol which is bridged by hydrogen bonds, and the organic compounds formed by crosslinking polymers by forming covalent bonds therebetween by heat, radiation, light, or plasma, or by addition of an organic cross linking agent.

Examples of inorganic compounds which form three-dimensional networks include metal oxides prepared by hydrolysis polycondensation of the metal alkoxides and layered clay minerals containing cations between layers. Inorganic gels composed of inorganic materials and water are formed from these inorganic compounds forming three-dimensional networks by aggregation of fine particles owing to their interactions.

Hydrogels made of inorganic materials are brittle and have low strength and elongation, and as a result, they are not generally used alone as hydrogel materials. In contrast, since hydrogels made of organic materials, particularly hydrogels composed of water and three-dimensional network of polymers formed by covalent bonds, have superior mechanical properties to inorganic gels, the application of these organic gels is under development in a wide range of industrial fields such as soft materials or functional materials.

In order to expand availability of the organic hydrogels, the provision of new types of organic hydrogels, which further exhibit the superior properties of the organic compounds in a more effective manner, is being investigated to improve homogeneity, transparency, dynamic and mechanical properties, and absorption (water absorption) properties of these gels.

In the electrophoresis, which has been widely used in the fields of chemistry, biochemistry, and medical care, filter paper, which has been used in the past as the electrophoresis medium (membrane), has recently been replaced with a polyacrylamide type hydrogel (hydrogel membrane obtained by crosslinking the polyacrylamide-type polymer using a polymer cross linker) due to its high performance. However, this hydrogel membrane has drawbacks in its characteristics such as low flexibility and fragileness due to its brittleness. In order to reduce the brittleness of the polymer gel membrane, a few measures have been proposed, one of which is to add agarose to the gel membrane (Japanese Patent (Granted) Publication No. Hei 4-77264) and the other one is to add a tri-functional organic cross linker (Japanese Patent Granted Publication No. Hei 4-77868). However, a further improvement in the toughness of the membrane is required.

In aqueous solution absorbent materials used for absorbing aqueous solutions such as physiological products, paper diapers, or other absorbent materials for absorbing body fluids, hydrogels with further improved absorptive properties and the mechanical characteristics of a gel are still required due to continuing advances of social activities of women and the aging of society. Although a few measures has been proposed, one of which is to bridge the surfaces of pulverized absorbing polymers using a cross linker (Japanese Patent (Granted) Publication Nos. Sho 60-18690, Sho61-48521, Hei 6-39487, Hei 6-74331, and U.S. Pat. No. 5,314,420), and another of which is to use trimethylolpropane triacrylate as the cross linker (WO 94/20547), further improvements in the absorbing property and the strength of the hydrogel remain necessary.

SUMMARY OF THE INVENTION

An object of the present invention is to provide a novel organic/inorganic hybrid hydrogel, a manufacturing method therefor and the dry body thereof. The organic/inorganic hybrid hydrogel of the present invention exhibits superior homogeneity, transparency, mechanical properties, water absorbing property, swelling and shrinkage properties, and the dry body of the organic/inorganic hybrid hydrogel is obtained by removing the water content of the hydrogel. The present invention was obtained by a series of experimental studies by the present authors and provides a novel hydrogel (hereinafter, called an organic/inorganic hybrid hydrogel) by incorporating water contained in a three-dimensional network by combining polymers and clay minerals at a molecular level, wherein the hydrogel includes a water soluble polymer and a water swelling clay mineral which can be homogeneously dispersed in water as essential constituent components.

That is, the present invention provides an organic/inorganic hybrid hydrogel which contains a water soluble polymer (A), a water swelling clay mineral (B) which can be homogeneously dispersed in water, and water (C), wherein the component (C) is contained in a three-dimensional network composed of the components (A) and (B).

In the above organic/inorganic hybrid hydrogel, the weight ratio of the water swelling clay mineral (B) to the water soluble polymer (A) is within a range of 0.01 to 10.

In the above organic/inorganic hybrid hydrogel, the water soluble polymer includes polymers obtained by polymerization of acrylamide derivatives and/or methacrylamide derivatives.

In the above organic/inorganic hybrid hydrogel, said organic/inorganic hybrid hydrogel has a critical temperature (Tc) and the state of said organic/inorganic hybrid hydrogel is reversibly changeable between the transparent and/or the volume swollen state at the lower temperature side and the opaque and the volume shrunken en state at the higher temperature of the critical temperature.

In the above organic/inorganic hybrid hydrogel in water, the volume ratio of which in water at temperatures below or beyond the critical temperature is equal to or more than 10.

In the above organic/inorganic hybrid hydrogel, the tensile load at break is equal to or more than 0.1N, the tensile elongation at break is equal to or more than 100%, and the load when the tensile elongation is 100% is more than 0.01N, in the case of using said organic/inorganic hybrid hydrogel, with a water content, defined by $\{C/(A+B)\}$ is 600 to 1000 weight % and with an initial sectional area is 0.237 $cm^2$.

In the above organic/inorganic hybrid hydrogel, the water content $\{Cmax/(A+B)\}\times100$ at the equilibrium swollen state is equal to or more than 2000 weight %.

In the above organic/inorganic hybrid hydrogel, the total transmission of visible light is equal to or more than 80%, in the case of using a 25 mm thick sample of said organic/inorganic hydrogel containing water (C) at 10 times (weight basis) higher than the content of the organic polymer (A).

The present invention provides a dry body of the hydrogel obtained by drying the above organic/inorganic hybrid hydrogel.

The present invention provides an organic/inorganic hybrid hydrogel for use as a membrane for electrophoresis.

The present invention provides aqueous solution absorbent materials formed by the organic/inorganic hybrid hydrogel and/or the dry body of the organic/inorganic hybrid hydrogel.

The present invention provides a manufacturing method of an organic/inorganic hybrid hydrogel comprising the steps of preparing a homogeneous solution containing (A') which corresponds to a monomer of an water soluble polymer (A), and a water swelling clay mineral (B) which can be homogeneously dispersed in water, and water (C), and polymerizing the monomer (A') under the presence of the clay mineral (B).

In the above manufacturing method, the homogeneous solution containing (A'), (B), and (C) further comprises an organic solvent which is miscible with water.

In the above manufacturing method, the weight ratio of the water swelling clay mineral (B) to the monomer (A') of the water soluble polymer (A) is within a range of 0.01 to 10.

In the above manufacturing method, the monomer (A') of the water soluble polymer includes acrylamide derivatives and/or methacrylamide derivatives.

The organic/inorganic hybrid hydrogel manufactured by the above manufacturing method has a critical temperature (Tc) and when the temperature increases or decreases crossing the critical temperature, the state of the hydrogel changes reversibly between the low temperature state, in which the gel is transparent and/or the volume swelling state, and when the temperature is higher than the critical temperature, the gel changes to the opaque and shrinking state.

The above manufacturing method provides said organic/inorganic hybrid hydrogel, the volume ratio of which in water at temperatures below or beyond the critical temperature is equal to or more than 10.

The manufacturing method provides said organic/inorganic hybrid hydrogel, in which the tensile breaking load is equal to or more than 0.1N, the tensile breaking elongation is equal to or more than 100%, and the load when the tensile breaking elongation is 100% is more than 0.01N, in the case of using a sample of the hydrogel whose water content, defined by $\{C/(A+B)\}$ is 600 to 1000 weight %, and whose initial sectional area is 0.237 $cm^2$.

The above manufacturing method provides the organic/inorganic hybrid hydrogel, in which the water content $\{Cmax/(A+B)\}\times100$ at the equilibrium swelling time is equal to or more than 2000 weight %.

The above manufacturing method provides said organic/inorganic hybrid hydrogel, in which the total transmission in the visible light range is equal to or more than 80%, in the case of using a 25 mm thick sample containing 10 times more of the water (C) (weight basis) than the polymer (A).

DETAILED DESCRIPTION OF THE INVENTION

Figure 1:
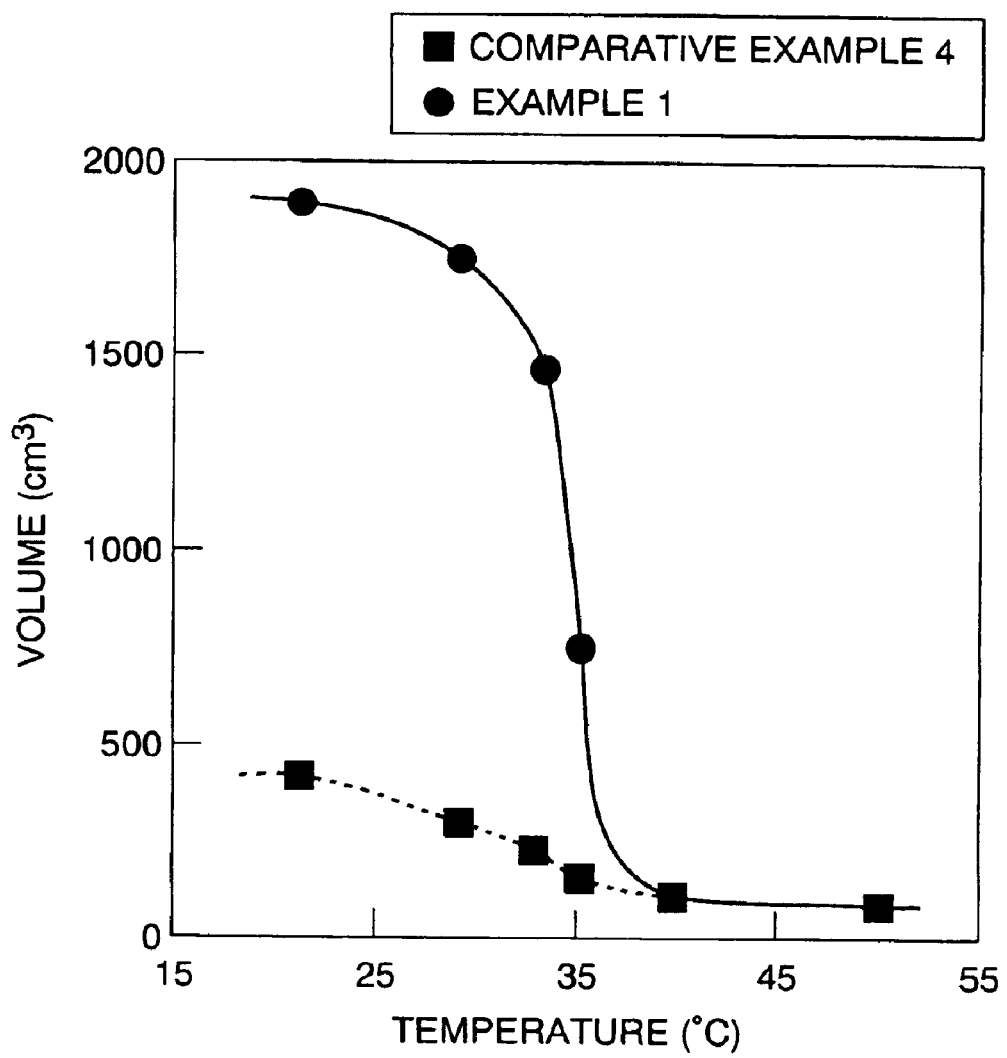
FIG. 1 is a diagram showing the temperature dependent volume changes in water of the organic/inorganic hybrid hydrogel obtained in Example 1 and the crosslinked organic hydrogel obtained in Comparative Example 4, when they are in the swollen state and in the shrunken state.

The water soluble polymers (A) of the present invention include not only water soluble polymers but also polymers which have a swelling property with respect to water. The polymers of the present invention include polymers, which become water soluble and water swelling only when particular conditions are met, such as the polymer concentration, the temperature, the pressure, or the presence of other additives. The water soluble polymers include polymers formed by one type of monomer or polymers formed by a plurality of types of monomers.

The water soluble polymers (A) in the present invention are preferably interactive with the water swelling clay minerals, which are homogeneously dispersable in water (B). The water soluble polymers preferably have functional groups which can form hydrogen bonds, ionic bonds, and coordinate bonds, and covalent bonds with the water swelling clay minerals (B).

Examples of polymers having such functional groups includes polymers having an amide group, an amino group, a hydroxy group, a tetramethyl ammonium group, a silanol group, and an epoxy group. The water soluble polymers used in this invention preferably have particular functions such that their polymer characteristics such as their hydrophilic properties or a hydrophobic properties change remarkably as a result of a small temperature change passing through the LCST (Lower Critical Solution Temperature).

Practical examples of the water soluble polymers include water soluble polymers obtained by polymerization of one or a plurality of compounds containing acrylamide, N-substitution acrylamide derivatives, N,N-di-substitution acrylamide derivatives, N-substitution metacrylamide derivatives, and N,N-di-substitution methacrylamide derivatives. A combination of the above-described monomers and the other organic monomers may be used as a polymer for forming an organic/inorganic hybrid hydrogel.

Examples of such water soluble polymers include poly (acrylamide), poly(N-methylacrylamide), poly(N-ethylacrylamide), poly(cyclopropylacrylamide), poly(N-isopropylacrylamide), poly(methacrylamide), poly(N-methylmethacrylamide), poly(cyclopropylmethacrylamide), poly(N-isopropylmethacrylamide), poly(dimethylacrylamide), poly(N,N-dimethylaminopropylacrylamide), poly(N-methyl-N-ethylacrylamide), poly(N-methyl-N-isopropylacrylamide), poly(N-methyl-N-n-propylacrylamide), poly(N,N-diethylacrylamide), poly(N-acryloylpyrrolidine), poly(N-acryloylpiperidine), poly(N-acryloylmethylhomopiperidine), poly(N-acryloylmethylpiperadine).

The water soluble polymers (A) used in the present invention include not only polymers which are soluble and swell with water but also those which are soluble and swell with a combination of water and organic solvents. The mixture of water and organic solvents is formed by water and one or a plurality of organic solvents, which are soluble in water.

Examples of organic solvents include methanol, acetone, methyl ethyl ketone and tetrahydrofuran. The mixing ratio of water to the organic solvent can be optionally selected within a range wherein the water swelling clay (B) can be homogeneously dispersed.

The water swelling clay mineral (B), which can be homogeneously dispersed in water and which is used in the present invention, is a type of clay mineral which can be dispersed homogeneously in water, and particularly preferable are layered clay minerals which can be dispersed in water at a molecular level (a single layer) or at a level close to the molecular level. Examples of such water swelling clay minerals includes water swelling smectite and water swelling mica. Practical examples are water swelling hectorite which contains sodium as an interlayer ion, water swelling montmorillonite, water swelling saponite, and water swelling synthetic mica. The water swelling clay minerals of the present invention are required to be dispersable in a homogeneous and fine manner, and it is preferable for the water swelling clay minerals to be dissolved in an aqueous solution. Here, the dissolution of the clay minerals means that there is no precipitate of the clay minerals or no coarse mineral aggregate to form a turbid solution. A more preferable type is a clay mineral which can be dispersed as nanometer thick particle within 1 to 10 layers and the most preferable type is a clay which can be dispersed as 2 layer thick particles.

The water (C) used in the present invention as one of the constituents is water or a combination of water and organic solvents which can be dissolved in water, and the present invention uses the organic solvents which can homogeneously disperse the water swelling clay minerals and the organic monomers. When the mixture of water and the organic solvents is used for dispersion, although the gel products include the organic solvent in addition to the water, these gel products are collectively called hydrogels for convenience.

The organic/inorganic hybrid hydrogel of the present invention is essentially formed by introducing water (C) into the three-dimensional network formed by (A) and (B). That is, the present invention is characterized in that a three-dimensional crosslinked structure containing water is formed by hybridization at the molecular level of (A) and (B) in water by crosslinking (A) by (B) or by crosslinking (B) by (A). That is, the organic/inorganic hybrid hydrogel of the present invention can be formed without using an organic cross linker and the present hydrogel exhibits superior characteristics which differ from those of the organic polymer crosslinked hydrogel (hereinafter, called an organic crosslinked hydrogel) obtained by polymerization of organic polymers by addition of an organic cross linker.

The organic/inorganic hybrid dry body of the present invention is obtained by drying the organic/inorganic hybrid hydrogel which is first formed by the manufacturing method of the present invention, and the dry body of the present invention has superior characteristics as shown below.

For example, as shown in Comparative Examples 5 to 8, even if a water solution of (A) and (B) is prepared, if a three-dimensional network composed of (A) and (B) containing water (C) is not formed at the molecular level, the organic/inorganic hybrid hydrogel of the present invention cannot be obtained, even if the composition of constituents is the same as that of the present invention.

It is possible to select any compositional ratio of the water soluble polymer (A) to the water swelling clay (B) which is homogeneously dispersed in water, if the organic/inorganic hybrid hydrogel is prepared and the compositional ratio of these two constituents (A) and (B) is not necessarily limited and can be variably selected depending on the types of the polymer (A) and the clay mineral (B). However, from the points of view of ease of synthesis and homogeneity of the hydrogel, a preferable weight ratio of B/A is within a range of 0.01 to 10, and a more preferable range lies within 0.03 to 2.0, and the most preferable range is selected within 0.1 to 1.0. When the weight ratio of B/A is less than 0.01, a satisfactory gel characteristics are not necessarily obtained, and when the ratio is more than 10, the obtained hydrogel is tends to be brittle and much of water is consumed in the manufacturing process, which causes production problems.

In contrast, the weight ratio of (C) to the sum of (A+B) can be optionally set to a wide range from 0 to a large value by adjusting the water content in the polymerization process and by swelling or drying in the subsequent process. The maximum water content, that is, the maximum water absorption value (Cmax), contained in the organic/inorganic hybrid hydrogel according to the present invention varies with the types and ratios of the constituents (A) and (B), and environmental conditions such as temperature and pH. The organic/inorganic hybrid hydrogel of the present invention is characterized in that the amount of Cmax contained in the present hydrogel is higher than that in conventional organic crosslinked hydrogels.

In general, Cmax (the equilibrium swelling water absorption value) increases as the ratio of B/A increases. The maximum water absorption Cmax of water (C) is measured by holding the organic/inorganic hybrid hydrogel in excess water under a particular conditions. For example, when an organic/inorganic hybrid hydrogel synthesized at a given water content is held in excess water at 20° C., and the hydrogel further absorbs water and the hydrogel reaches an equlibrium swelling value (the maximum swelling value) at 20° C.

Accordingly, the time dependency of the swelling property and the equilibrium swelling value are obtained by taking out the hydrogel immersed in excess water and by measuring the water absorption of the hydrogel. As described above, the equilibrium swelling value [{Cmax/(A+B)}×100] of the hydrogel varies with the type and composition of the constituents A and B and with environmental conditions such as temperature, pH and salt concentration, and the equilibrium value may vary from a low value of 100 wt % to a high value of 100,000 wt %.

The organic/inorganic hybrid hydrogel of the present invention has the feature that the equilibrium value Cmax thereof is far higher than that of a conventional organic crosslinked hydrogel. The equilibrium swelling value [{Cmax/(A+B)}] of the organic/inorganic hybrid hydrogel of the present invention is preferably equal to or more than 2,000 wt %, and more preferably equal to or more than 3,000 wt %, and, most preferably equal to or more than 4,000 wt %.

The other feature of the organic/inorganic hybrid hydrogel of the present invention is that the swelling speed is far higher than that of conventional organic crosslinked hydrogels. Presumably, the higher swelling rate is obtained because the three-dimensional network of (A) and (B) is homogeneously formed so as not to hinder the water absorption. In addition, as described later, the organic/inorganic hybrid hydrogel of the present invention has the feature that it has a high swelling speed as well as a high shrinking speed due to temperature changes, when the organic polymer (A) in the present hydrogel has both swelling and shrinking properties due to temperature changes.

As described later, the organic/inorganic hybrid hydrogel of the present invention has a excellent dynamic and mechanical properties in spite of the high equilibrium value Cmax and the high swelling speed thereof.

The organic/inorganic hybrid hydrogel of the present invention includes a hydrogel having a critical temperature (Tc) and the transparency or the volume of the hydrogel show a reversible change when the temperature changes up and down passing through the critical temperature.

Such organic/inorganic hybrid hydrogels of the present invention are prepared using a polymer having a LCST (Lower Critical Solution Temperature) in the aqueous solution. The critical temperature Tc of the organic/inorganic hybrid hydrogel is the same as or differs from the LCST of the polymer.

The organic/inorganic hybrid hydrogel products obtained by the present invention includes hydrogel products which show at least one or all of the features of a higher water absorption value and higher transparency; and a higher volume change and transparency change due to temperature changes which passes through the critical temperature; and a higher changing speed of the volume and transparency due to temperature changes which passes through the critical temperature, when compared to conventional organic crosslinked hydrogels.

For example, in an organic crosslinked hydrogel, when the concentration of the cross linker is increased for increasing the degree of crosslinking, the crosslinking becomes inhomogeneous and sometimes the transparency of the organic hydrogel is lost. (Comparative Example 4, and T. Tanaka, Scientific American Vol. 244, pp. 110 to 123, 1981). In contrast, in the organic/inorganic hybrid hydrogel of the present invention, even if the same polymer is used, the homogeneity is not lost and the transparency is maintained high. In practice, in a 25 mm thick sample of the organic/inorganic hybrid hydro-sol, which contains an amount of water (C) ten times (weight basis) higher than the water soluble polymer (A), the transmission of visible light is preferably more than 80%, and more preferably more than 85%, and most preferably 90% or more. In the dry body of the organic/inorganic hybrid hydrogel, the transparency can be maintained because of the presence of the finely dispersed water swelling clay mineral.

Figure 2:
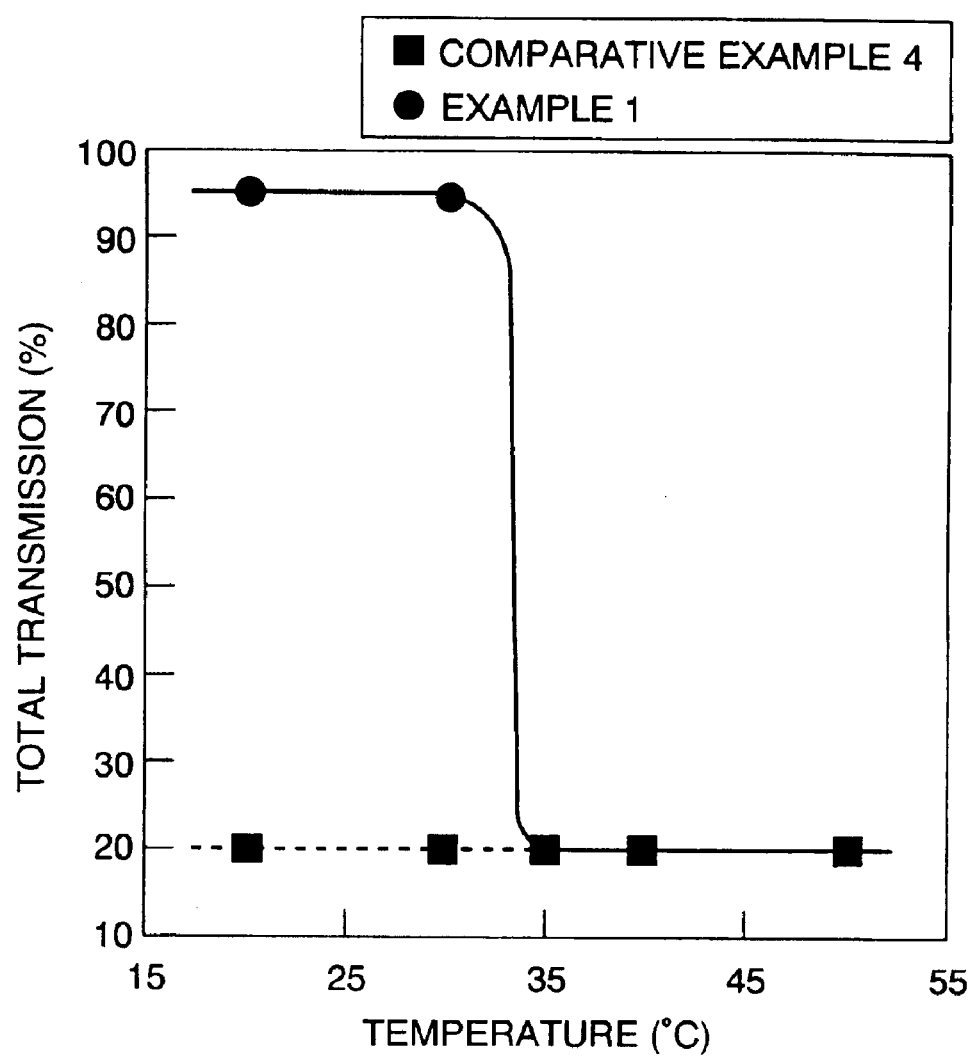
FIG. 2 shows the temperature dependent transparency change of the organic/inorganic hybrid hydrogel obtained in Example 1 and the crosslinked organic hydrogel obtained in Comparative Example 4.

As shown in FIG. 1, the transparency of the organic crosslinked hydrogel having a low crosslinking density does not show any remarkable change for the change of temperatures which passes through the critical temperature Tc. In contrast, the transparency of the organic/inorganic hybrid hydrogel according to the present invention, whose crosslinking density is high, shows a remarkable change due to changes in temperature which passes through the critical temperature Tc in addition to its superior mechanical properties As shown in FIG. 2, the organic/inorganic hybrid hydrogel (Example 1) according to the present invention has the characteristic feature that it shows a remarkable volume changes due to swelling and shrinkage due to temperature changes passing through the critical temperature Tc in contrast to the small volume change observed for organic crosslinked hydrogels (Comparative Example 4) for the same temperature change near the critical temperature Tc. The ratio of the volume in the swollen state to the shrunk state with respect to the organic/inorganic hybrid hydrogel of the present invention can be optionally set according to the objective of the invention. In general, the organic/inorganic hybrid hydrogel of the present invention has a far larger ratio of the volume change from the swollen state to the shrunken state than the same volume change ratio of the organic crosslinked hydrogel. The organic/inorganic hybrid hydrogel products obtained according to the present invention are provided with volume change ratios from the swollen to the shrunken states of preferably 10 times, more preferably 20 times, and most preferably 30 times larger than that of the organic crosslinked hydrogel.

The organic/inorganic hybrid hydrogel products of the present invention include those having superior mechanical properties in mechanical strength, elongation, and toughness. The feature of the present invention is that the organic/inorganic hybrid hydrogel according to the present invention includes those which are excellent in mechanical properties in addition to those superior in water absorption, transparency, and drastic changes of the volume and the transparency due to temperature changes which pass through the transition temperature. The mechanical properties of the organic/inorganic hybrid hydrogel products vary with water content thereof, thus the properties of the organic/inorganic hybrid hydrogel products of the present invention are represented for those containing water within a defined range. In practice, the measured values are obtained by the measurement of the organic/inorganic hybrid hydrogel products, in which the value of {C/(A+B)}×100 is within a range of 600 to 1000, that is, the content of water (C) is 600 to 1000 weight % of organic plus inorganic components (A+B), or those containing ten times of water (C) than the water soluble polymer (A).

Furthermore, since the organic/inorganic hybrid hydrogel products of the present invention have large tensile elongation values at break, the cross-sectional area changes during testing, and test samples for measuring the elongation at break are formed so as to have a cross-sectional area (initial cross-sectional area) of 0.237 cm$^2$, which corresponds to a circle having a radius of 0.275 cm.

That is, measurements for the organic/inorganic hybrid hydrogel products of the present invention are performed using test samples in which the water content defined by $\{C/(A+B)\} \times 100$ is within a range of 600 to 1000 weight %, and the initial cross-sectional area is 0.237 cm$^2$. The measurements of the organic/inorganic hybrid hydrogel products of the present invention showed that the tensile loads at break of the present hydrogel products ranges from more than 0.1N, preferably more than 0.5N, more preferably more than 1N, and most preferably more than 2N.

The tensile elongation tests at break of the organic/inorganic hybrid hydrogel products were performed using the same test samples containing the above water contents and having a cross-sectional area of 0.237 cm$^2$. The tensile elongation tests at break showed that the obtained values of the tensile elongation at break of the present hydrogel products are included in a range of more than 100%, in a preferable range of more than 200%, in a more preferable range of 300%, and in the most preferable range of 500%. The organic/inorganic hybrid hydrogel products of the present invention with respect to a tensile load at an elongation of 100% include hydrogel products having preferably more than 0.01N, more preferably more than 0.05N, and most preferably more than 0.1N.

In contrast, the organic crosslinked hydrogel products shown in Comparative Examples 4, and 9 to 12 are far weaker than those of the organic/inorganic hybrid hydrogel of the present invention and almost all of the test samples of the organic crosslinked hydrogel products were too weak to be mounted on the test chuck of the tension test machine, and even if the test sample could be mounted, the samples broke immediately after starting the test and no test results were obtained.

The organic/inorganic hybrid hydrogel of the present invention showed favorable mechanical properties during the absorption of water, and the samples showed sufficient toughness to withstand the tensile tests. In practice, the test samples containing water having a diameter of 5.5 mm and a length of 30 mm were used for evaluating the deformation resistances of the organic/inorganic hybrid hydrogel products of the present invention. The test results showed that the preset hydrogel products include those which resisted being broken while being subjected to compressive deformation to one third (⅓), and preferably one fifth (⅕) of their original thickness, and resisted being broken while subjected to an elongation deformation of more than 2 times, preferably 4 times of their original length, and resisted being broken while being subjected to a bending deformation of bending to more than an angle of 100 degrees, preferably 150 degrees, at the center of the test sample. In contrast, the test samples of the organic crosslinked hydrogel, which used an organic crosslinking agent in place of the water swelling inorganic clay, were not resistant to all or any one of deformations, and all of the test samples of the organic crosslinked hydrogel broke or failed.

The organic/inorganic hybrid hydrogel of the present invention must form a three-dimensional network constituted by an organic polymer and a clay mineral, and the hydrogel products of the present invention are manufactured by the following method. A homogeneous water solution including a monomer (A') of a water soluble polymer (A), a water swelling clay mineral (B), and water (C) is prepared, and the monomer (A') is polymerized under the presence of (B). Thereafter, a fine hybridization of (A) and (B) at the molecular level is achieved and an organic/inorganic hybrid hydrogel is formed by gelling of the three-dimensional network.

In practice, the manufacturing method of the organic/inorganic hybrid hydrogel comprises the steps of preparing a water solution containing essential constituents of (A'), (B), and (C), and executing radical polymerization of (A') under the presence of (B), which is finely dispersed in water. In this manufacturing method, the clay mineral (B), dispersed finely preferably at a level of 1 to 10 layers and more preferably at a nanometer level of 1 to 2 layers, plays the role of a crosslinking agent of (A'), so that a three-dimensional network of (A)+(B) is formed in water. The above-described radical polymerization can be performed by known methods under existence of peroxide and/or ultraviolet light irradiation excluding molecular oxygen. The polymerization reaction can be accelerated by heating and/or by ultraviolet light irradiation.

A suitable radical polymerization initiator and a catalyst for the radical polymerization can be selected from the groups of known radical polymerization initiators and catalysts. Preferable radical polymerization initiators and preferable catalysts are those which are water soluble and can be dispersed homogeneously in water. Examples of the polymerization initiators includes a water soluble peroxide, such as potassium peroxodisulfate, ammonium peroxodisulfate; water soluble azo compounds such as VA-044, V-50, V-501 (products of Wako Chemicals Co. Ltd.); and a water soluble radical initiator having poly(ethylene oxide) chains.

Preferable examples of catalysts include N,N',N'-tetramethylethylenediamine and β-dimethylaminopropionitrile.

The polymerization temperature is optionally set to a temperature ranging from 0° C. to 100° C. in conformity with the type of initiators and catalysts. The polymerization time period varies with the type of catalyst and initiator, and polymerization conditions such as the polymerization temperature and the amount of polymerization solution (concentration), and the polymerization times are within a range of several ten of seconds to several hours. In order to execute homogeneous polymerization in the water solution system, it is effective to prepare the water solution by first preparing a homogeneous water solution of (B), adding a polymerization initiator after dissolving it in the water solution of (A'), and then adding a polymerization catalyst dissolved in water.

In the above radical polymerization reaction, it is possible to manufacture the organic/inorganic hybrid hydrogel in the form of fine particles by further addition of a surface active agent.

In the polymerization reaction for manufacturing the organic/inorganic hybrid hydrogel, the polymerization yield of (A') is high and the water soluble polymer obtained by the polymerization reaction is included inside the hydrogel together with the clay mineral, so that the water soluble polymer included in the gel is not likely to be eluted. This is confirmed by the high polymerization yield after rinsing the reaction product with water. Such a high polymerization yield in the polymerization under the presence of (B) is presumably obtained because the finely dispersed clay layered particles act as an effective crosslinking agent for the water soluble polymer.

Furthermore, in order to improve the characteristics of the organic/inorganic hybrid hydrogel, an organic crosslinking agent may be introduced in the water solution composed of the essential constituents of (A') and (B). The concentration of the organic crosslinking polymer introduced into the solution is not limited and the concentration can be selected to meet the objective of the invention. Examples of organic crosslinking agents which may be introduced into the solution include bi-functional compounds which are conventionally known, such as N,N'-methylenebisacrylamide, N,N'-propylenebisacrylamide, di(acrylamidemethyl)ether, 1,2-diacrylamodeethyleneglycol, 1,2-diacrylamide ethyleneglycol, 1,3-diacryloyletgyleneurea, ethylediacrylate, N,N'-diallyltartardiamide, and N,N'-bisacrylylcystamine; and tri-functional compounds such as triallylcyanurate, and triallylisocyanurate.

In manufacturing the organic/inorganic hybrid hydrogel of the present invention, it is possible to manufacture hydrogels having various shapes by changing the shape of the container. The organic/inorganic hybrid hydrogel can be prepared in various shapes such as a fiber shape, a rod-shape, a plate-shape, a cylindrical shape, a spiral shape, and a spherical shape. Organic molecules such as anioionic surface active agents, organic dyes, and organic pigments; and organic polymers such as water soluble polymers, water insoluble fibrous materials, and inorganic fine particles such as carbon, silica, or titan oxide can be introduced in any of the manufacturing steps of the organic/inorganic hybrid hydrogel and into its dry body in any manufacturing steps thereof, and it is also possible to hybridize (disperse and laminate) the hydrogel together with other materials.

The present invention also includes a dry body which is obtained by removing the water content from the hydrogel. The method for removing the water content in the hydrogel is not limited, and drying can be executed by changing the temperature, flowing gas, and reducing the pressure. In practice, a dry air circulating dryer or a pressure reduction dryer are used. The amount of water being removed from the hydrogel is not limited, and various type of dry gel can be obtained as required, from a completely dried dry body to a dry body containing a necessary amount of water. Although the dry body of the organic/inorganic hybrid hydrogel of the present invention includes a powdered clay mineral, the powder is so fine that the dry body can be transparent. Accordingly, when the hydrogel or the dry body absorbs a colored solution, it is a feature of the present invention that the degree of absorption of the colored solution can be detected by the light transmission or by the light reflection. When other organic or inorganic components are dispersed in the hydrogel, the advantage of the present invention is that the degree of dispersion can be easily and clearly detected.

The hydrogel, the half-dry gel, and the dry body of the organic/inorganic hybrid hydrogel can be pulverized, classified, and molded into any shape suitable for transportation, processing, and application. In practice, these gel materials are converted into the shapes of balls, scales, powders, films, fibers, and pellets. The powder size, for example, generally is in a range of 10 to 1,000 $\mu$m, but is not limited thereto. The dry body of the organic/inorganic hybrid hydrogel of the present invention can be restored reversibly to the original hydrogel by contacting with water, an aqueous solution, or moisture. This novel organic/inorganic hybrid hydrogel can be widely used in the field of live units, medical care, medicine, agriculture, civil engineering, and industrial fields.

The organic/inorganic hybrid hydrogel and/or the dry body thereof of the present invention is useful as the fluid absorbing material of sanitary products. The present hydrogel and its dry body are provided with the characteristics, required for sanitary products such as menstrual products or paper diapers, since the hydrogel and/or its dry-body of the present invention have favorable properties such as a high water absorption capability, a high water absorbing speed, and a high mechanical toughness after absorbing water, and, furthermore, the favorable properties extend to long-term mechanical stability of the hydrogel after absorbing water and very small elution of the water soluble components from the hydrogel.

As aqueous solution absorbent materials, the organic/inorganic hybrid hydrogels and/or the dry gel products thereof according to the present invention can be used alone or in combinations with other materials such as other water soluble polymers, hydrophilic polymers, hydrophobic polymers, surface active agents, or other inorganic fillers.

The organic/inorganic hybrid hydrogels and/or the dry gel products thereof according to the present invention can be used in various shapes such as particles, scales, and films, and can be used integrated with other materials, or by incorporating various components such as anionic ion surfactants (for example, alkylsulfate), denaturants such as uric acid and formaldehyde, antioxidents (for example, 2-2-mercaptoethanol), water soluble polymers (for example, polyvinylalcohol, polyethyleneglycol), agarose, wetting agents (for example, glycerin), disinfectants, colorants, flavoring agents, deodorants, inorganic powders, and organic fibers.

The aqueous solution absorbent materials and the dry gel products thereof according to the present invention can be effectively applied to sanitary products such as paper diapers and sanitary napkins. In such sanitary applications, it is preferable to use the aqueous absorbent materials in conventionally known forms as sanitary products used on the market. For example, a surface of paper diapers is covered by a sheet of porous and hyrophobic nonwoven fabric in order to prevent the baby skin from being irritated, and below the surface layer, a floffy pulp layer is disposed as a primary absorbent material for improving the absorption speed, and inside the diaper, the aqueous solution absorbent material of the present invention is arranged so as to be tightly adhered with the primary absorbing layer in the form of power or thin films for increasing the absorbing amount.

In addition, by use of a stretchable rubber band or adhesive tape, the periphery of a paper diaper is gathered so as to prevent urine from escaping from the diaper.

In the sanitary napkins, the aqueous solution absorbent material of the present invention is used by first pulverizing into powder, mixing the powder with pulp to form a sheet, then laminating the sheet with rayon pulp, and the surface is further covered by a nonwoven fabric or polyethylene laminated paper, so as to form a structure such that blood and body fluids can be absorbed rapidly.

Since the organic/inorganic hybrid hydrogel and/or its dry body have superior dynamic and mechanical properties, superior ease of processing and handling, the present hydrogel membrane is favorably used as a medium for electrophoresis.

The organic polymer content in the acrylamide/inorganic hybrid hydrogels and/or the dry gel products thereof according to the present invention for use as electrophoresis media is not limited, but it is preferable that the acrylamide polymer content in the hydrogel ranges from 2 to 30 weight %. In the case of containing an organic crosslinking agent, a sum of the acrylamide polymer and the organic crosslinking agent is used as the polymer content in the hydrogel.

Although an concentration of the water swelling clay mineral used in the polyacrylamide-type hybrid hydrogel used for the electrophoresis media cannot be generally defined because the concentration of the clay mineral differs depending on types or concentrations of the organic acrylamide compounds, the concentration preferably ranges from 0.5 to 500 weight %, more preferably from 5 to 300 weight %, and most preferably from 10 to 200 weight %.

A transparent and colorless hydrogel is preferably used as the electrophoresis media. This transparent hydrogel is obtained by using a type of clay mineral, which can be dispersed homogeneously in the hydrogel. The transparency of the hydrogel used for the electrophoresis media is preferably more than 80% in total transmission in the visible range, more preferably more than 90%, and most preferably 95%.

If the transparency of the electrophoresis medium is less than 80% due to inhomogeneous dispersion of the clay mineral or inhomogeneous crosslinking due to the effect of a coexisting crosslinking agent, detection of the electrophoresis pattern becomes inaccurate.

The gel electrophoresis media according to the present invention may include other components for use as the electrophoresis media. Examples of such components include denaturants such as anionic surfactants (for example, alkylsulfate), uric acid, or formaldehyde; an antioxidant (for example, 2-mercaptoethanol), a water soluble polymer (for example, polyvinylalcohol, polyethylene glycol), agarose, and a wetting agent (for example, glycerin).

The gel electrophoresis media according to the present invention may include a pH buffer solution for buffering PH of the sample solution (for example, potassium dihydrogenphosphate-disodium hydrogenphosphate).

When the hydrogel of the present invention is used as a layer or as a membrane, the hydrogel membrane can be formed by coating a gel forming solution by a known method on a flat and smooth support plate such as a glass plate having hydrophilic surfaces or a plastic sheet (for example, polyethylene terephthalate) having hydrophilic surfaces, and then by polymerizing the gel forming solution. The polymerization of the gel forming solution can be executed in a temperature ranging from 0 to 100° C. and is easily executed at temperature ranging from room temperature to 80° C.

The polymerization time cannot be specified because the time is dependent on the polymerization time or the thickness of the gel membrane. However, the polymerization is completed within several minutes to several hours. When the gel solution coated on the support plate is polymerized, the surface of the coat can be covered by a cover film or a sheet. It is also possible to mount the electrophoresis medium after polymerization on a support plate.

The gel media according to the present invention can be applied to the horizontal and vertical plane electrophoresis methods as well as the disc-type electrophoresis method, and the hydrogel electrophoresis media is advantageously used in the electrophoretic analyses of biopolymers such as DNA or proteins.

Embodiments

The present invention will be explained in detail by the following Examples. However, it is noted that the present invention is not limited to the following examples.

EXAMPLE 1

A water swelling synthetic hectorite having a composition of $[Mg_{5.34}LiO_{0.66}Si_8O_{20}(OH)_4]Na^+_{0.66}$ (Trade Name, Raponite XLG: Japan Silica Co. Ltd.) was used after drying at 100° C. for 2 hours. As a polymer, N-isopropylacrylamide (IPAA: Kojin Co. Ltd.) was used after refining by recrystallization in a mixed solvent composed of toluene and hexane (1/10 weight ratio) into colorless needle crystals.

Peroxodisulfate potassium (PPS: Kanto Chemicals Co. Ltd.) was diluted in water at a ratio of PPS/water=0.384/20 (g/g) and the water solution of PPS was used as the polymerization initiator. N,N,N',N'-tetramethylethylenediamine (TMEDA: Kanto Chemicals Co. Ltd.) was diluted in water at a ratio of TMEDA/water=160 $\mu$l/20 g and this solution was used as a polymerization catalyst. Purified water was used in every manufacturing process after distillation of ion exchanged water and then after removing the included oxygen by bubbling high purity nitrogen for more than three hours.

In a thermostatic chamber, 16.96 g of purified water and a stirring rod made of Teflon were introduced into a flat bottom glass container having an inside diameter of 25 mm and a length of 80 mm. While stirring, 0.662 g of Raponite XLG was added gradually while taking care to avoid entraining bubbles in the solution.

Subsequently, 2.0 g of IPAA was added and stirred for 5 minutes and a hyaline solution is obtained. Subsequently, 1.06 g of the PPS solution and 2.0 g of TMEDA solution were added while stirring, and after further stirring for about 15 sec, a colorless and transparent solution (D) is obtained. A part of the solution (D) is transferred to three glass tubular containers each having an inside diameter of 5.5 mm and a length of 150 mm with a sealed bottom preventing oxygen from entering the solution, and each container top was sealed tightly and these containers were held still at 20° C. for 15 hours for polymerization.

The remaining solution (D) was held still in the flat bottom container at 20° C. for 15 hours for polymerization. All of these operations from preparation of the solution to polymerization were executed in a nitrogen atmosphere free of oxygen. Cylindrical gel products which are elastic, tough, colorless, transparent, and homogeneous, were formed in both flat bottom container and tubular containers, and these gel products were carefully transferred from the containers.

No heterogeneity or opaque aggregates by the clay minerals or the like were observed. It was confirmed, by drying the obtained gel products at 100° C. in a vacuum dryer until weight of the gel products becomes constant, that the obtained gel products are hydrogel products whose water content defined by $\{C/(A+B)\times100\}=750$ wt %.

These gel products were subjected to three refining operation, and the refined gel products were obtained as follows.

Three cycles of the refining operations were repeatedly conducted and one cycle is constituted by immersing the gel product in two liters of water for 2 days and then transferring for immersing in one liter of water at 70° C. for two hours. The refined gel products were dried at 100° C. under a reduced pressure and the dried hydrogel products, in which the water content was reduced, were obtained. It was confirmed that the dry hydrogel products can be restored to the same elastic hydrogel with the same shape as that of the original hydrogel before drying.

The dry gel products were subjected to a measurement using the Fourier Transform Infra-Red Absorption Spectrometer (Fourier Transform Infra-Red Spectrometer FT/IR-550, Japan Spectroscopy Co. Ltd.) and characteristic infrared absorption peaks for poly(N-isopropylacrylamide) (for example, 1460 $cm^{-1}$, 1550 $cm^{-1}$, 1650 $cm^{-1}$, 2920 $cm^{-1}$, and 2970 $cm^{-1}$) and for Raponite XLG (for example, 460 $cm^{-1}$, 650 $cm^{-1}$, and 1005 $cm^{-1}$) were observed.

Thermogravimetric analysis of the dry gel body was conducted using a thermogravimetric apparatus produced by Seiko Electronic Industrial Co. Ltd. by increasing the temperature at a rate of 10° C./min. up to 600° C., while flowing air, and a result of B/A=0.33 was obtained.

As described above, the gel obtained in this embodiment (Example 1) is the hydrogel composed of a polymer (poly (N-isopropylacrlamide)), a clay mineral, and water; the compositional ratio of the polymer and clay in the hydrogel was the same as that at the initial blending; the obtained hydrogel is colorless, transparent and homogeneous, although no crosslinking agent is used in the polymerization process; and the dry body (solid) obtained by removing water from the above hydrogel can be restored to its original shape by immersion in water. These results obtained in this embodiment suggest that the three-dimensional network is formed by hybridization of the polymer with the clay mineral at the molecular level. A hydrogel was not obtained under the same manufacturing conditions, with the exception being the exclusion of the clay mineral from the composition of Example 1.

A tension test was conducted using a rod-shaped unrefined organic/inorganic hydrogel (with a cross-sectional area of 0.237 cm$^2$) by mounting on a tension testing machine (the table-top type universal testing machine produced by Shimazu Works Ltd.) by a pair of chucks at a clearance of 20 mm at a tensioning rate of 100 mm/min. The test results showed that the tensile load at break is 1.1N, the tensile elongation at break is 550%, and the tensile load at a tensile elongation of 100% was 0.09 N.

A rod-shaped organic/inorganic hydrogel in 10 mm long was refined and immersed in water held at six temperatures ranging from 0 to 50° C., and the volume of sample was measured after maintaining in respective temperatures. The temperature dependent volume change of the hydrogel of Example 1 by swelling and shrinking is shown in FIG. 1 in addition to the volume change of the organic gel (organic crosslinking hydrogel) of Comparative Example 4.

As described above, the organic/inorganic hybrid hydrogel obtained in the present embodiment (Example 1) has a toughness and critical temperature (Tc), and the hydrogel swells at a temperature lower than the critical temperature Tc, and shrinks at a temperature higher than the critical temperature Tc. A very high volume ratio of 24 was obtained for the hydrogel of the present invention when the volume in the swollen state at 20° C. is compared with the volume in the shrinking state at 50° C.

After refining and after being immersed at five temperatures, the cylindrical organic/inorganic hydrogel produced in the flat bottom container was cut into flat disks with a thickness of 2 mm, and the optical transmission of the flat disk was measured using a transmissometer NDH-300A (Japan Densyoku Kogyo Co. Ltd.) and the temperature dependent transmission changes are shown in FIG. 2 along with the result for the sample obtained in the Comparative Example 4. As shown in FIG. 2, the organic/inorganic hybrid hydrogel obtained in the present embodiment (Example 1) showed a clear change in the temperature dependent transparency at the critical temperature Tc, and the hydrogel of the present invention was highly transparent at temperatures lower than Tc and at temperatures higher than Tc, the hydrogel became opaque.

EXAMPLES 2 to 4

Organic/inorganic hybrid hydrogels were prepared with the same composition and the same manufacturing method as those of Example 1 except that the amount of clay mineral (Raponite XLS) was replaced with 0.132 g (Example 2), 0.264 g (Example 3), and 1.322 g (Example 4).

The evaluation results of the hydrogel products evaluated by the same methods as those used in Example 1 are shown below. The water contents defined by $\{C/(A+B)\}$ were 940 weight % (Example 2), 880 weight % (Example 3), and 600 weight % (Example 4), and the ratios of B/A of these gel products were 0.065 (Example 2), 0.135 (Example 3), and 0.65 (Example 4).

When the temperature of the hydrogel products were increased, it was confirmed that the respective hydrogel products had critical temperatures Tc at around 35° C., and respective hydrogel products showed volume shrinkage and transparency loss above the critical temperature. The volume ratio of the hydrogel products before and after shrinkage at 20° C. to 50° C. were 31 (Example 2) and 41 (Example 4). Shrinkage at the critical temperature was occurred very rapidly, within one minute, and swelling also occurred within a comparatively short time. The tension tests of these hydrogel products showed that the tensile loads at break were 0.65N (Example 3) and 7.0N (Example 4), the tensile elongation values at break were 430% (Example 3) and 650% (Example 4), and the loads at the elongation of 100% were 0.033 N (Example 3) and 0.40N (Example 4).

The water contents of hydrogel products defined by $\{C_{max}/(A+B)\}$ in the equilibrium swollen state at 20° C. were 11300 weight % (Example 2), 7200 weight % (Example 3) and 5000 weight % (Example 4).

EXAMPLES 5 to 7

Various polymers for manufacturing the organic/inorganic hybrid hydrogel examples were used such as IPAA for Example 5, N,N-dimethylacrylamide (DMMA: Wako Chemicals Co. Ltd.) for Example 6, and N,N-diethylacrylamide (DEAA: Wako Chemicals Co. Ltd). Note that DMAA and DEAA were used after removing the polymerization inhibitor by passing a silica-gel column using an 80 ml volume of silica gel for 100 ml of each organic polymer.

In a thermostatic chamber, 18.96 g of pure water and a stirring rod were put into a flat bottom glass container with an inside diameter of 25 mm and a length of 80 mm, the inside of which is replaced with nitrogen. While stirring, 0.662 g of Raponite XLG was gradually added while taking care to avoid entraining bubbles for preparing a transparent solution. Then, 2.0 g of IPAA (Example 5), 2.0 g of DMAA (Example 6), and 2.0 g of DEAA (Example 7) were added to the above solution and these solutions were stirred until they become transparent. Subseqently, 160 μl of TMEDA was added, and 1.06 g of PPS solution was added while stirring, and a hyaline solution (D') was obtained. The stirring rod was removed from the hyaline solution (D') and after sealed tightly, the solution was maintained still at 20° C. and the solution was gelled, and the content did not move even when the container was lain on its side. All of the above operations were performed in the absence of oxygen. Subsequently, the gelled solution was allowed to stand still for two hours at 70° C. in a nitrogen atmosphere for polymerization. After two hours, the cylindrical gel was carefully transferred from the container.

In Examples 5 and 7, elastic, tough, and opaque gel products were obtained, and in Example 6, an elastic, tough, and transparent gel product was obtained. In the opaque gel products, aggregates of the clay mineral and the like were not observed.

The water contents defined by $\{C/(A+B)\} \times 100$ measured similarly to Example 1, for each sample was the same, i.e., 750 weight %, and the products were identified as organic/ inorganic hydrogel products composed of a organic polymer, a clay mineral, and water. The hydrogel products obtained in Examples 5 and 7 did not become transparent by reducing the temperature. The hydrogel obtained in Example 6 did not become opaque even when the temperature was raised to 70° C.

EXAMPLES 8 to 12

As the polymers for constituting the hydrogel products, N-isproplyacrylamide (IPAA) was used in Example 8, and in place of IPAA, N,N-dimethylacrylamide (DMAA) in Example 9, N,N-diethylacrylamide (DEAA) in Example 10, acryloylmrpholine (ACMO: Koj in Co. Ltd.) in Example 11, and N,N-dimetylaminopropylacrylamide (DMAPA) in Example 12 were respectively used. Toluene in an amount of 0.75 times (weight basis) of IPAA (Example 8) was added to IPAA, the IPAA was dissolved at 40° C., and after returning to the room temperature, hexane in an amount of 0.75 times of IPAA was added, and needle like colorless crystals of IPAA were obtained, which were used for synthesis of the hydrogel. DMAA (Example 9), DEAA (Example 10), and AMCO (Example 11) were used after removing the polymerization inhibitor, similar to the cases of Examples 6 and 7. In addition, DMAPA (Example 12) was used upon removing the polymerization inhibitor by passing through an active alumina column (80 cc/100 ml monomer) after addition of acetone in an amount of 20 volume % of DMAPA for reducing the viscosity, and then removing the acetone by a rotary evaporator.

Purified water was used in every manufacturing process after the distillation of ion-exchanged water and after removing included oxygen by bubbling high purity nitrogen for more than three hours. It is noted that all of the operations before polymerization (preparation of the raw material solution to the transfer of the hydrogel products) were performed in a nitrogen atmosphere after removing oxygen and flowing nitrogen. In addition preparations of the catalyst solution and the initiator solution were also executed in a nitrogen atmosphere intercepting oxygen.

85.3 g of purified water and a stirring rod were put into a two neck flask placed in a water bath at 20° C. and 2.98 g of Raponite XLS was gradually added into the flask while stirring so as not to entrain bubbles, obtaining a transparent solution. Subsequently, after addition of each polymer such as 9.0 g of IPAA (Example 8), 9.0 g of DMAA (Example 9), 9.0 g of DEAA (Example 10), 9.0 g of ACMO (Example 11), and 9.0 g of DMAPA (Example 12), each solution was stirred until it became transparent. The weight ratio of the Rapponite XLS/inonomer was 0.331 in each solution. Subsequently, the flask was cooled in an ice bath, 72 μl of TMEDA, cooled separately, was added, and after stirring for 30 seconds, 4.77 g of the PPS solution, which was prepared similarly to Example 1 and cooled separately, was added while stirring, and a homogeneous transparent solution was obtained. These solutions were maintained still for 20 hours for completing polymerization in the flask in a water bath at 15° C. for 20 hours. The elastic hydrogel products, gelled a whole (did not move or flow even when the flask was laid on its side), were obtained in every Examples 8 to 12. No inhomogeneous portions or aggregates of opaque clay mineral or polymer particles were observed in the hydrogel products.

The transparency of the hydrogel samples after polymerization was visually examined in a water bath (1° C.) and the results showed that the hydrogel samples of Examples 8, 9, 11, and 12 were transparent but the sample of Example 10 was translucent. The visual light transmission of the hydrogel samples cut 25 mm thick were measured using a transmissometer NDH-300A (Japan Desyoku Kogyo Co. Ltd.).

The total transmission in the visible range of each hydrogel sample was 95% (Example 8), 81% (Example 9), 40% (Example 10), 85% (Example 11), and 90% (Example 12). The total transmission in the visible range was also measured at 50° C. for examining the change in the total transmission. At 50° C., the total transmissions of samples of Examples 9, 11, and 12 did not change but samples of Examples 8 and 10 were changed to be opaque.

The hydrogel products were cut into sample rods with a diameter of 5.5 mm, and a length of 50 mm. Compression tests to compress the sample to ⅓ to ⅕ of its original length in the longitudinal direction, tension tests to elongate the sample to two and four times of its original length in the longitudinal direction, and bending tests to bend the sample at its center point by 100 and 150 degrees and more, were carried out. In all of the compression, elongation and bending tests, no fractures, cracks, or defects were observed for the samples of these Examples and the samples were returned to their original shapes after the tests.

The hydrogel products were cut into sample rods with a diameter of 5.5 mm (cross-sectional area of 0.237 $cm^2$) and a length of 50 mm for the tension tests. The same universal testing machine as used in Example 1 was used and the sample rods were protected so as not to damage either end portion of the sample rod within 10 mm and the sample rod was mounted on the test machine by a pair of cylindrical shaped sand paper holders at a clearance of 30 mm, and the tension test for each sample rod was carried out at a tensioning rate of 100 mm/min. The test results showed that the product of Example 8 had a tensile load at break of 2.9N, a tensile elongation at break of 1001%, and a load at 100% elongation of 0.103N; the product of Example 9 had a tensile load at break of 2.4N, a tensile elongation at break of 1112%, and a load at 100% elongation of 0.089N; the sample of Example 10 had a tensile load at break of 4.8 N, a tensile elongation at break of 892%, and a load at 100% elongation of 0.173N.

The obtained hydrogel products were cut into 5 mm squares, and their water contents defined by {Cmax/(A+B)}×100 were evaluated after they were immersed in water inside a water container held in a Water bath at 20° C. to reach the equilibrium swelling. The results were 6200% (Example 8), 5000% (Example 9), 3700% (Example 10), and 4700% (Example 11).

The weight measurement of the dry gel body obtained by drying the refined hydrogel, similar to Example 1, showed that the polymerization yields of all gel products of Examples 8 to 11 are higher than 99%.

EXAMPLE 13

The polymerization and evaluation tests procedures conducted similarly to Example 8 except for using 3.15 g of acrylamide (Kanto Chemicals Co. Ltd.) after refining by use of ethanol and toluene as the organic monomer, 2.8 g of Raponite XLG as the water swelling clay mineral (the weight ratio of XLG/monomer=0.89), 50 g of water, 0.05 g of peroxodisulfate potassium as the initiator, 40 μl of N,N'-methylenebisacrylamide as the catalyst, and a polymerization temperature of 23° C. As a result, a transparent (the total transmission is 85% at 1° C. for a 25 mm thick sample) and tough organic/inorganic hybrid hydrogel was obtained. No transmission change was observed when the sample temperature was increased to 50° C.

EXAMPLE 14

The polymerization and evaluation tests were conducted similarly to Example 9 except for using 1.788 g of XLG as the clay mineral, an organic crosslinking agent (N,N'-methylenebisacrylamide: BIS, Kanto Chemicals Co. Ltd.) by 0.5 mol % of the organic monomer, and the polymerization temperature of 30° C. As a result, a transparent and tough organic/inorganic hybrid hydrogel was obtained. The total transmission at a temperature of 1° C. for a 25 mm thick sample was 90% and no transmission change was observed even when the temperature was increased to 50° C. No fracturing was observed in the various deformation tests such as the compression tests to compress the thickness of a sample rod of 5.5 mm in diameter and 30 mm in length into ⅕ of its original length, elongation tests to elongate a sample of the same size as mentioned above to four times of its original length in the longitudinal direction, and a bending test to bend a sample of the same size as mentioned above to 180 degrees. After these deformation tests, the hydrogel samples returned to their original shape.

EXAMPLES 15 to 17

The polymerization and evaluation tests were conducted similarly to the Example 2 except for using mixed solvents of water and methanol, wherein the mixing ratios (weight basis) of water to methanol were 80:20 (Example 15), 60:40 (Example 16), and 40:60 (Example 17), and the polymerization temperature was 15° C. The results of the polymerization experiments showed that, in each of Examples 15 to 17, transparent and tough hydrogel products were obtained which are composed of poly(N-isopropylacrylamide), XLG, water and methanol. The transparency was measured for each sample in an ice bath at a temperature of 1° C., and the sample of Example 15 was transparent, and the samples of Examples 16 and 17 were opaque, particularly, the sample of Example 17 was completely white. Subsequently, these hydrogel products were refined by purified water. After refining, the samples of the hydrogel products obtained in Examples 15 to 17 were swelled at 20° C. and tests were performed by increasing the temperature to determine whether the samples had critical temperatures. The test results showed that each of the samples of Examples 15 to 17 has a critical temperature at around 33° C. Each hydrogel is swollen and transparent below its the critical temperature Tc and shrunk and opaque above the critical temperature Tc. Above test results showed that the organic/inorganic hybrid hydrogel can be obtained when a mixture of water and an organic solvent is used. Thermogravimetric analyses of the dry gel bodies of the present Examples 15 to 17 showed that the ratio of B/A in weight basis was 0.06 in every sample.

EXAMPLES 18–21

Polymerization operations were carried out similarly to Example 8 (Example 18), Example 9 (Example 19), Example 10 (Example 20), and Example 11 (Example 21), except for changing the polymerization temperature to 50° C. Tough, transparent, and homogeneous organic/inorganic hybrid hydrogel products were obtained. At the polymerization temperature immediately after polymerization, the hydrogel products of Examples 19 and 21 were transparent, but the hydrogel products of Examples 18 and 20 were white and opaque. When the temperature as reduced to 1° C., the hydrogel products of Examples 18, 19, and 21 became transparent, and the hydrogel of Example 20 became opaque or translucent. The samples of these hydrogel products cut into 25 mm thick discs showed a total transmission in the visible range of 84% (Example 18), 93% (Example 19), 30% (Example 20), and 88% (Example 21).

EXAMPLE 22

A homogeneous solution containing water (85.3 g), XLG (2.98 g), TMEDA (72 µl), and PPS (4.77 g water solution) was prepared similarly to Example 8, except for using as the organic monomers of 4.5 g of N-isopropylacrylamide (IPAA) and 3.94 g of N,N'-dimethylacrylamide, and the solution was polymerized at 15° C. An elastic, homogeneous, and translucent hydrogel was obtained. Inhomogeneous portions or aggregates of opaque clay minerals were not observed in the hydrogel. The temperature dependent transmission measurement for the sample of this hydrogel after cutting it into 25 mm thick discs showed a change (LCST) from a translucent state to an opaque state at 40 to 50° C. The sample of Example 8, which uses IPAA alone as an organic monomer, showed a rapid transition at 32 to 34° C. from a transparent state (total transmission of 90%) to an opaque state (total transmission of 6%). In contrast, the transition temperature increased and the transition became slow in the present sample of Example 22.

The obtained hydrogel was cut into sample rods with a diameter of 5.5 mm and a length of 30 mm. Using these sample rods, mechanical tests were performed such as the compression tests to compress the sample rods into ⅓ to ⅕ of their original length in the thickness direction, the elongation tests to elongate the samples to 2 to 4 times of the original length in the longitudinal direction, and bending tests to bend the sample at their center point by 100, 150, and more degrees. No fractures and no cracks were found in the sample rods of the present hydrogel products after the mechanical tests and the present hydrogel samples returned to the original shape after these mechanical tests.

EXAMPLES 23 and 24

The procedures were carried out similarly to Example 8, except that the amounts of the water swelling clay XLG and the organic monomer IPAA were changed to 2.98 g of XLG and 0.45 g of IPAA (the weight ratio of XLG/IPAA=6.62) in Example 23, and 0.0596 g of XLG and 4.5 g of IPAA (the weight ratio of XLG/IPAA=0.013) in Example 24. The results of experiments showed that homogeneous and transparent hydrogel products were obtained in Examples 23 and 24. The total transmissions of 25 mm thick samples of Examples 23 and 24 were 95.1% (Example 23) and 98.2% (Example 24).

EXAMPLES 25 and 26

The procedures were conducted similarly to Example 8 except that in Example 25, XLS was used (XLS containing pyrophosphoric sodium as a deflocculant by 6 weight % of XLS: Japan Silica Co. Ltd.) as the swelling inorganic clay mineral in place of XLG, and that in Example 26 a synthetic smectite was used (Corp Chemical Co. Ltd.) as the water swelling clay mineral in place of XLG. Homogeneous raw material solutions were prepared in both Examples 25 and 26, and transparent hydrogel products were obtained in Examples 25 and 26. The total transmissions for 25 mm thick samples were 90.4% (Example 25) and 83.8% (Example 26).

EXAMPLE 27

A homogeneous solution was prepared composed of 6.3 g of acrylamide after refining in ethanol and toluene, 6.8 g of XLG after drying at 100° C. for 2 hours, 0.1 g of peroxodisulfate potassium, 80 μl of TMEDA, and 100 g of water. The oxygen which was saturated and dissolved in the water and the solution was removed by nitrogen bubbling. The above-described homogeneous solution was uniformly coated to form a 300 μm thick film on a 180 μm thick poly(ethylene terephtalate)(PET) sheet (support), whose surfaces were made hydrophilic in advance. When this coated film is polymerized at 28° C. a homogeneous and transparent gel film was obtained, although the solution contained no organic crosslinking agent. The total transmission of the film was 92%. A sample filler port was formed in the gel film using a cutter. A sample slot with a sharp section was obtained, and no breaking of the film and no cracking was observed around the port.

Then, the gel film was covered with a PET film (a 100 μm thick cover film), whose surface was made hydrophilic, and a medium for electrophoresis was obtained. Using this gel film, electrophoresis tests were performed with respect to a standard protein (cytochrome C (molecular weight 12400)), chymotorypsinogen A (molecular weight 2500), ovalbumin (molecular weight 45000), and bovine serum albumin (molecular weight 67000). The electrophoresis media were stained by immersing them in a 0.1% comassie blue stain and the separation performance of the gel membrane was visually examined. Sharp separation patterns were obtained as a result.

COMPARATIVE EXAMPLE 1

The polymerization was conducted at 20° C. for 15 hours using the same composition as that of Example 1 except that the clay mineral was excluded. In the flat bottom glass container is well as the tubular glass containers, transparent solutions of poly(N-isoprpylacrylamide) in water were obtained, but no hydrogel products were obtained. When the temperature of the solutions were increased to more than 32° C., opaque polymer-gel products in the state separated from water were obtained. However, when the temperature was decreased to 20° C., the partially gelled solution was returned to the original solution.

The organic polymer formed in the solution was analyzed by diluting the solution in 5 liters of water, maintaining it in a water tank at 50° C. for collecting opaque aggregates of the dissolved polymer, and separated by centrifugal separation (20° C., 10,000 rpm, for 60 min.), and analyses (measurements of infra-red absorption spectrum and nuclear magnetic resonance spectrum) of the separated sample were made after refining by reprecipitation using water, acetone, and hexane.

COMPARATIVE EXAMPLE 2

The polymerization was conducted similarly to Comparative Example 1 except that the raw material solution was changed to pH 11 by addition of NaOH. Similarly to the comparative Example 1, no gel product was obtained except for obtaining a colorless transparent solution. As a result, the increase of pH accompanied by the addition of the clay mineral, observed in Example 1, does not affect on the polymerization of organic monomers.

COMPARATIVE EXAMPLES 3 and 4

The polymerization was carried out similarly to Example 1, except that no clay mineral was used and that, after addition of IPAA, an organic crosslinking agent was added in an amount of 1 mol % of IPAA (Comparative Example 3) and 5 mol % of IPAA (Comparative Example 4) in the raw material solution. N,N'-methylenebisacrylamide (BIS) (Kanto Chemicals Co. Ltd.) was used without processing as the organic crosslinking agent. In Comparative Example 3, a colorless and transparent gel product was obtained, and in Comparative Example 4, an opaque gel product was obtained.

The same measurements as for Example 1 showed that the water contents defined as {C/(A+B)}×100 were 990 weight % (Comparative Example 3) and 935 weight % (Comparative Example 4), and that an organic crosslinked hydrogel products were formed.

The temperature dependency tests showed that the hydrogel sample of Comparative Example 3 had a critical temperate at around 33° C. and the hydrogel sample was in the swollen state at temperatures below Tc, and in the shrunken state at temperatures above Tc. The ratio of the volume in the swollen state to that in the shrunken state was around 8. In contrast, the hydrogel sample of the Comparative Example 4 was opaque, and this sample also shoved a volume change from the swollen state below the Tc of 33° C. to the shrunken state above the Tc, and the ratio of the volume change was around 5.

The volume change and the total transmission change from 20° C. to 50° C. for the organic hydrogel product obtained in Comparative Example 4 are illustrated together with those changes of the organic/inorganic hydrogel of Example 1 in FIGS. 1 and 2.

COMPARATIVE EXAMPLES 5 and 6

0.331 g (Comparative Example 3) or 0.066 g (Comparative Example 4) of the clay mineral (Raponite XLG) was added while stirring to the solution of Comparative Example 1, which is a solution of 1 g of poly(N-isopropylacrylamide) in 10 g of water. Although an attempt was made to form organic/inorganic hybrid hydrogel products having the same compositions as those of Examples 1 and 2, homogeneous and tough hydrogel products could not be obtained.

COMPARATIVE EXAMPLE 7

A mixed solution prepared by adding 0.2 g of the clay mineral (Raponite XLG) dissolved in 9.8 g of water as gradually added while stirring to a transparent solution having the same composition as that of Comparative Example 1, except for containing a DEAA monomer by adding 0.15 g of poly(N,N'-(diethylacrylamide) dissolved in 14.85 g of water. When the water solution of the XLG clay is added to an amount of 0.88 g (B/A=0.117), white floating particles were separated, and the solution became gradually opaque. Even when the XLG solution was continuously added until the amount of the XLG solution reached 3.88 g (B/A=0.517), the mixture remained a cloudy solution.

These cloudy solutions were inhomogeneous solutions containing white floating aggregated particles, and when heated, the cloudiness of these solutions increased at temperatures above 28° C. However, in either case, no homogeneous hydrogel products were obtained. Even when the amount of the clay mineral or the amount of polymer were increased, no homogeneous and tough hydrogel products were obtained.

COMPARATIVE EXAMPLE 8

A mixture of the polymer, the clay, and water was prepared having similar compositions to that of Example 7 except that 10 g of poly(N,N'-diethylacrylamide) was gradually added to the XLG solution. The addition of DEAA makes this solution cloudy and even by heating to a temperature above the critical temperature Tc, no homogeneous and tough hydrogel product was obtained.

COMPARATIVE EXAMPLES 9 to 12

The polymerization of several sample solutions was conducted by maintaining at 15° C. for 20 hours, similarly to Examples 10 or 11, except that the clay mineral was not used and, after DEAA (Comparative Examples 9 and 10) or ACMO (Comparative Examples 11 and 12) were added, an organic crosslinking agent N,N'-methylenebisacrylamide, was added in an amount corresponding to 1 mol % of DEAA or ACMO (Comparative Examples 9 and 11) or 5 mol % of DEAA or ACMO (Comparative Examples 10 and 12). In every case of Comparative Examples 9 to 12, the hydrogel products formed by gelation of the whole content in the container were obtained. No inhomogeneous aggregate was observed. The transmission tests of respective hydrogel samples examined at 1° C. showed that the hydrogel products of Comparative Examples 9 and 11 are homogeneous and transparent but the hydrogel samples of Comparative Examples 10 and 12 were opaque. The total transmissions of these samples measured by an NDH-300 transmissometer (Japan Densyoku Kogyo Co. Ltd.) were 98% (Comparative Example 9), 24% (Comparative Example 10), 98% (Comparative Example 11), and 22% (Comparative Example 12).

Rod-shaped organic crosslinked hydrogel samples were produced by polymerizing solutions of Comparative Examples 9 to 12 in polymerization containers with an inside diameter of 5.5 mm and a length of 150 mm. These rod gel products were cut into samples with a length of 30 mm and subjected to various deformation tests such as compression tests to compress these sample rods to ⅓ of the original thickness, elongation tests to elongate these sample rods to two times their original length, and bending test to bend these sample rods at their center to 100 degrees. As a result, the sample rods cracked, broke, or failed. Furthermore, tension tests were attempted using sample rods with an inside diameter of 5.5 mm and the length of 150 mm. It was attempted to mount these sample rods on the same universal testing machine as that used in Example 1 using a pair of cylindrical sand paper chucks, but almost all of the sample rods were broken. Some samples were mounted on the testing machine by the chucks with an interval of 30 mm, but these samples broke immediately after starting the tension test at a tensioning rate of 100 mm/min, so that no characteristic data was obtained.

COMPARATIVE EXAMPLES 13 and 14

The rod shaped hydrogel samples Comparative Examples 13 and 14 were produced in glass tube containers with all inside diameter of 5.5 mm and with a length of 150 mm similar to Comparative Example 3 in the case of Comparative Example 13 and similar to Comparative Example 4 in the case of Comparative Example 14. The obtained hydrogel rods were cut into 30 mm length, and these 30 mm long sample rods were subjected to various deformation tests such as compression test to compress the sample to the ⅓ of its original thickness, elongation tests to elongate them to 2 times their original length, and bending tests to bend to 100 degrees. The sample rods of Comparative Examples 13 and 14 broke, cracked, or failed. The hydrogel rods were cut into 50 mm long sample rods and the tension tests of these sample rods were attempted using the same universal testing machine by mounting these sample rods with a pair of cylindrical sand-paper holders separated at an interval of 30 mm. However, these sample rods were too brittle to mount on the testing machine so that no data was obtained.

The present invention provides a novel organic/inorganic hybrid hydrogel which has superior properties such as high homogeneity, high transparency, high mechanical and dynamic properties, high water absorbing capability, high swelling and high shrinking properties, an a manufacturing method therefor, and a dry gel body which is obtained by drying the novel organic/inorganic hybrid hydrogel. There are various types of organic/inorganic hybrid hydrogel products obtained according to the present invention, including a tough and high tension hydrogel, a transparent or uniformly white hydrogel, a hydrogel which is reversible from the transparent and swollen state below the critical temperate (Tc) to the opaque and shrunken state above Tc. The hydrogel products are favorably used as a medium for electrophoresis. The dry gel body of the organic/inorganic hybrid hydrogel can be easily restored to a hydrogel and, owing to its high water absorbing capability; the dry gel body is favorably used for liquid absorbing sanitary goods.

What is claimed is:

1. A manufacturing method for an organic/inorganic hybrid hydrogel comprising the steps of:
preparing a homogeneous solution containing (A') which corresponds to a monomer of a water soluble polymer (A), a water swelling clay mineral (B) which can be homogeneously dispersed in water, and water (C); and
polymerizing the monomer (A') under the presence of the clay mineral (B) such that after polymerization the organic/inorganic hybrid hydrogel has a tensile load at break of more than 0.1N, a tensile elongation at break of more than 100%, and a load at a tensile elongation of 100% is more than 0.01N in the case of using said organic/inorganic hybrid hydrogel, having a water content defined by $\{C/(A+B)\}$ is 600 to 1000 weight %, for a sample which has an initial sectional area of 0.237 $cm^2$.

2. A manufacturing method for an organic/inorganic hybrid hydrogel according to claim 1, wherein said homogeneous solution containing (A'), (B), and (C) further comprises an organic solvent which is miscible with water.

3. A manufacturing method for an organic/inorganic hybrid hydrogel according to claim 1, wherein the weight ratio of the water swelling clay mineral (B) to the monomer (A') of the water soluble polymer (A) is within a range of 0.01 to 10.

4. A manufacturing method for an organic/inorganic hybrid hydrogel according to claim 1, wherein said water soluble polymer (A) includes polymers obtained by polymerization of acrylamido compounds and/or methacrylamido compounds.

5. A manufacturing method for an organic/inorganic hybrid hydrogel comprising the steps of:
preparing a homogeneous solution containing (A') which corresponds to a monomer of a water soluble polymer (A), a water swelling clay mineral (B) which can be homogeneously dispersed in water, and water (C); and
polymerizing the monomer (A') under the presence of the clay mineral (B),
wherein said organic/inorganic hybrid hydrogel has a critical temperature (Tc), at which the organic/inorganic hybrid hydrogel changes reversibly between the transparent and swollen state at a lower temperature of the critical temperature and an opaque and shrunken state at a higher temperature of the critical temperature.

6. A manufacturing method for an organic/inorganic hybrid hydrogel according to claim 5, wherein the volume ratio of said organic/inorganic hybrid hydrogel in water below the critical temperature to that above the critical temperature is equal to 10 or more.

7. A manufacturing method for an organic/inorganic hybrid hydrogel comprising the steps of:

preparing a homogeneous solution containing (A') which corresponds to a monomer of a water soluble polymer (A), a water swelling clay mineral (B) which can be homogeneously dispersed in water, and water (C); and polymerizing the monomer (A') under the presence of the clay mineral (B), wherein the water content defined by {Cmax/(A+B)} of said organic/inorganic hybrid hydrogel in the equilibrium swollen state is equal to or more than 2000 weight %.

8. A manufacturing method for an organic/inorganic hybrid hydrogel comprising the steps of:

preparing a homogeneous solution containing (A') which corresponds to a monomer of a water soluble polymer (A), a water swelling clay mineral (B) which can be homogeneously dispersed in water, and water (C); and polymerizing the monomer (A') under the presence of the clay mineral (B), wherein a total transmission in the visible range of said organic/inorganic hybrid hydrogel is more than 80%, when a 25 mm thick sample of said organic/inorganic hydrogel containing water (C) at 10 times (weight basis) higher than the content of an polymer (A) is used.

* * * * *